US012714298B2

(12) United States Patent
Mowlai-Ashtiani et al.

(10) Patent No.: US 12,714,298 B2
(45) Date of Patent: Aug. 25, 2026

(54) LAVAGE AND CLEANSING SYSTEM AND METHOD

(71) Applicant: Medtronic Xomed, Inc., Jacksonville, FL (US)

(72) Inventors: Ali Mowlai-Ashtiani, Jacksonville, FL (US); Phillip Berman, Jacksonville, FL (US)

(73) Assignee: Medtronic Xomed, Inc., Jacksonville, FL (US)

(*) Notice: Subject to any disclaimer, the term of this patent is extended or adjusted under 35 U.S.C. 154(b) by 416 days.

(21) Appl. No.: 17/082,815

(22) Filed: Oct. 28, 2020

(65) Prior Publication Data

US 2022/0125288 A1 Apr. 28, 2022

(51) Int. Cl.
*A61B 1/12* (2006.01)
*A61B 1/00* (2006.01)
*A61B 1/018* (2006.01)

(52) U.S. Cl.
CPC .......... *A61B 1/126* (2013.01); *A61B 1/00039* (2013.01); *A61B 1/00068* (2013.01); *A61B 1/018* (2013.01)

(58) Field of Classification Search
CPC ... A61B 1/126; A61B 1/0039; A61B 1/00068; A61B 1/018; A61B 1/015; A61B 1/00135; A61B 2217/005
See application file for complete search history.

(56) References Cited

U.S. PATENT DOCUMENTS 3,835,842 A * 9/1974 Iglesias .................. A61B 1/307 600/105
3,865,842 A * 2/1975 Robba .................. C07D 333/60 546/202
5,392,765 A * 2/1995 Muller .................. A61B 1/307 600/156
9,345,386 B1 5/2016 Cheng
2010/0331620 A1* 12/2010 Sohn .................. A61B 17/3423 600/104
2014/0318582 A1* 10/2014 Mowlai-Ashtiani .......................... A61B 1/00135 134/166 C
2015/0087907 A1 3/2015 Konstorum et al.
2015/0087908 A1 3/2015 Cheng et al.
2015/0087911 A1 3/2015 Konstorum et al.
2016/0174828 A1* 6/2016 Drach ............... A61B 1/00128 600/123
2016/0199548 A1 7/2016 Cheng
2017/0127917 A1* 5/2017 Cheng ............... A61B 1/00135
2020/0375444 A1* 12/2020 Coffeen ............ A61B 1/00128

* cited by examiner

*Primary Examiner* — Michael J Carey
*Assistant Examiner* — Megan Elizabeth Monahan
(74) *Attorney, Agent, or Firm* — Carter, DeLuca & Farrell, LLP

(57) ABSTRACT

A fluid delivery system may be positioned relative to a scope to assist in cleaning a scope and/or lavaging a portion of a subject during a procedure. The fluid delivery system may include a sleeve positioned over a portion of a scope. The sleeve may include passages and/or define passages relative to the scope.

13 Claims, 9 Drawing Sheets

LAVAGE AND CLEANSING SYSTEM AND METHOD

FIELD

The subject application relates to a lavage and/or cleansing system, and particularly to a sleeve system for a scope.

BACKGROUND

This section provides background information related to the present disclosure which is not necessarily prior art.

In a selected procedure, a viewing instrument may be used to view a portion of a subject. For example, a scope may be used to view a portion of a nasal cavity during a selected procedure, such as a debridement or resection thereof. The scope may be passed through a nasal portion into a sinus cavity and/or to view the nasal cavity. The scope, therefore, may be used by the user, such as a surgeon, to view internal portions of a subject.

The scope, however, may become covered with material that is removed from the subject during a procedure. The material may include tissue, blood, and other material. Therefore, viewing through the scope may be obstructed during a procedure. The user may, therefore, be required to remove the scope from the subject and clean the scope to allow for appropriate viewing of the surgical area.

SUMMARY

This section provides a general summary of the disclosure, and is not a comprehensive disclosure of its full scope or all of its features.

A cleaning or cleansing system may be positioned relative to a scope to assist in cleaning a scope during a procedure. The cleaning system may include a sleeve that may be positioned over a portion of an endoscope and may be provided as separate from a scope, such as a laparoscope or an endoscope. The sleeve may include one or more passages and/or define passages relative to an endoscope for a selected procedure.

The sleeve may include a passage to allow a flow of a fluid to a terminal or viewing end of the endoscope. The passage may direct fluid for cleaning or cleaning an area relative to the end of an endoscope. Thus, the sleeve may allow for cleaning an endoscope viewing portion of an endoscope.

Further, the sleeve may define one or more passages relative to the endoscope. The passages may allow for irrigating or lavaging an area during a procedure. Various passages may also allow for removal or suction of material relative to the scope.

Therefore, a sleeve may be provided relative to a scope, such as an endoscope. The sleeve may allow for cleaning the endoscope during use without removing the endoscope from the subject. Further, the sleeve may allow for at least one of providing a fluid for cleaning a surgical area and/or suction from a surgical area to assist in cleaning and viewing the surgical area.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
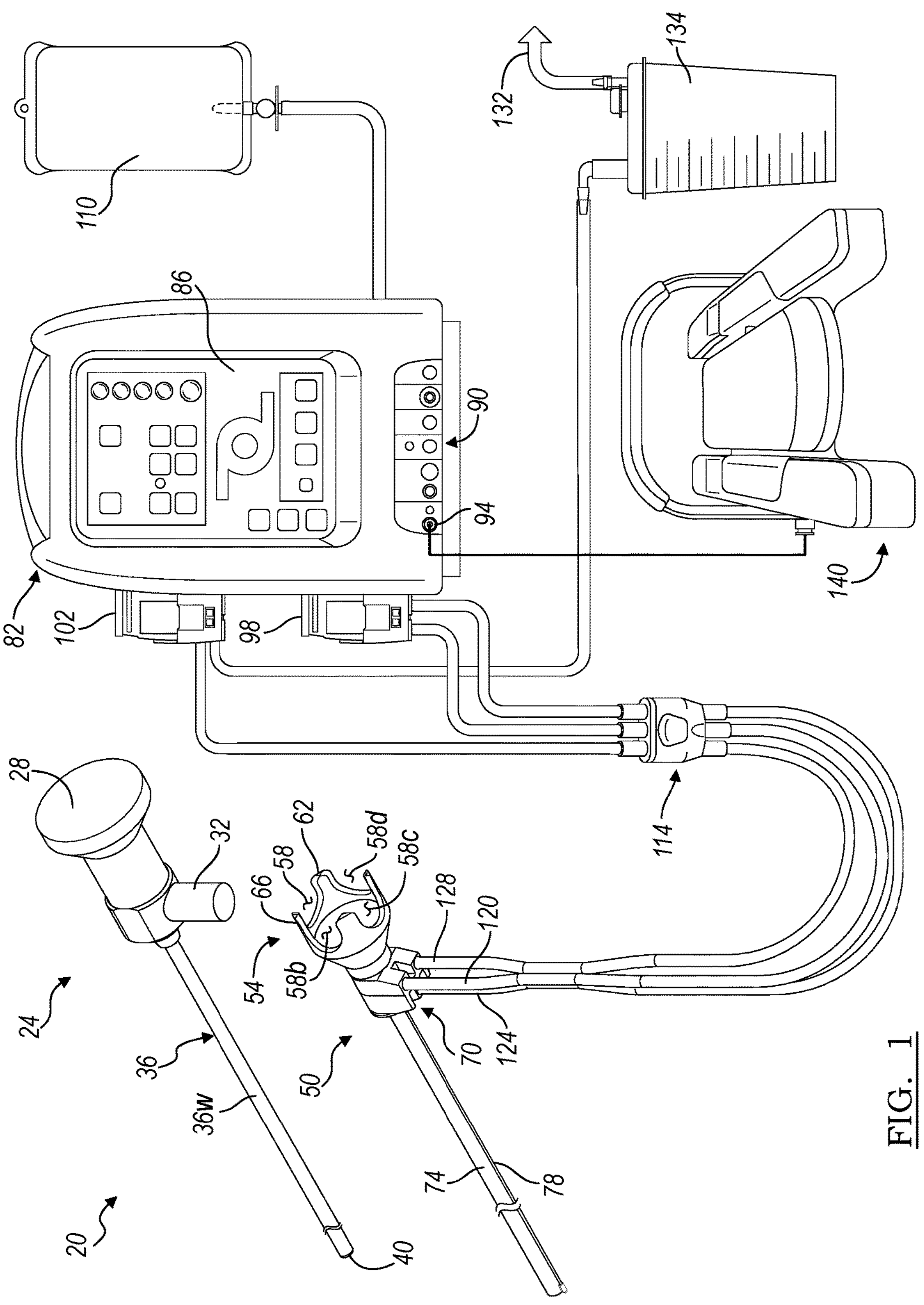
FIG. 1 is a schematic view of a scope and sheath system, according to various embodiments.

With initial reference to FIG. 1, a cleansing or cleaning system 20 is illustrated. The cleansing system 20 may include various portions, including those discussed further herein. The cleansing system 20 may include portions for at least one of cleaning, lavage, suction, etc.

Generally, the cleansing system 20 may be operated relative to and/or include a selected scope 24. The scope 24 may be any appropriate scope, such as an endoscope, laparoscope, or the like. In various embodiments, for example, the scope 24 may include an endoscope such as a Sharpsite® endoscope sold by Medtronic, Inc., and/or Medtronic ENT, having a place of business in Minnesota and/or Florida. It is understood, however, that the scope 24 may be any appropriate scope. Further, the scope 24 is not required for provision and/or operation of all or parts of the cleansing system 20.

Generally, the scope 24 may include a viewing area or portion 28 and a lighting portion or connection 32. The lighting portion or section 32 may provide light to a distal end or through a scope tube 36. The scope tube 36 may include a distal end 40 through which a view of a surgical or operational area is made. The distal end 40 may include a lens or portion to view through the viewing end 28. The lens or distal portion 40 may become obstructed during use, as discussed further herein.

The system 20 may further include a sheath assembly 50. The sheath assembly 50 may include a scope connection region or portion 54. The scope connection portion 54 may include or one or more depressions or passages 58 formed between selected projections, such as projections 62 and 66.

The depression 58 may be positioned relative to the scope 24, such as to allow for passage or engagement with the light connection 32. The sheath assembly 50, therefore, may include a plurality of the depressions 58 to allow for arrangement of the sheath assembly 50 relative to the scope 24 and a plurality of positions. As illustrated in FIG. 1, the sheath 50 may include four depressions, designated 58*a*, 58*b*, 58*c*, and 58*d*.

The sheath may further include a fluid connection or passage member or portion 70. The fluid connection 70 may form or provide paths, as discussed herein, to direct fluid relative to portions of the sheath assembly 50. The sheath assembly 50 further includes a scope tube cover 74 and a cleaning fluid passage 78. The scope tube cover 74 and the cleaning fluid passage 78 may both for formed or provided as elongated members extending to a distal end, as discussed. The sheath assembly 50 may be positioned relative to the scope 24, as discussed further herein.

The system 20 may further include a control assembly or panel 82. The control assembly 82 may include various control portions, and/or inputs and/or outputs. In various embodiments, the control assembly 82 may include an input screen 86, which may be a touch screen. It is understood that various soft buttons may be displayed on the touch screen 86 to allow for input from the user or from a selected user. In various embodiments, various hard buttons may also be provided. The control system may include a processor or processor module to execute selected instructions for operation of the system 20, as discussed herein. A memory may also be provided that stores the selected instructions. The inputs may be used to select what operations to perform. Additionally, the control system 82 may include selected outputs, such as one or more ports 90. The ports 90 may include a power port 94 which may include power for the light connection 32 to allow for powering a light of the scope 24. The control assembly 82 may include the integrated power console or powered console IPC® system, sold by Medtronic, Inc.

The control console 82 may also assist in controlling or allowing control of fluid flow through various portions of the sheath 50, as discussed further herein. Accordingly, the console 82 may include a pump 98 and/or control the pump 98. The control console 82 may further include a valve system or portion 102. The pump 98 may pump fluid from a source 110, such as a saline bag, fluid storage area, or the like. Nevertheless, the pump 98 may pump fluid though a fluid delivery system or assembly 114. The fluid may flow from the source 110 through the fluid delivery system 114 to one or more ports or connections of the sheath 50. For example, the sheath 50 may include a cleaning connection 120. The sheath 50 may also or alternately include a lavage or rinsing connection 124. The sheath 50 may further interconnect to a suction or vacuum port 128 to a suction or vacuum line 132 in line with the vacuum line and the vacuum portion 128 may be a vacuum canister or collection area 134. It is understood, however, that a collection canister 134 is not required. The control system 82 may further include the pinch valve or valve assembly 102 to selectively control a vacuum through the sheath 50. Thus, the sheath 50 may be provide and the system 20 operated to move and/or directed selected fluids as discussed herein.

The system 20 may include selected control mechanisms, including those discussed above such as the touch screen 86. In various embodiments, however, the system 20 may further include inputs or additional and/or alternative inputs 140. The input 140 may include a foot switch, hand switch, or the like. The input 140, for example, may be operated by a user to select one or more operations of the system 20, as discussed further herein.

Figure 2:
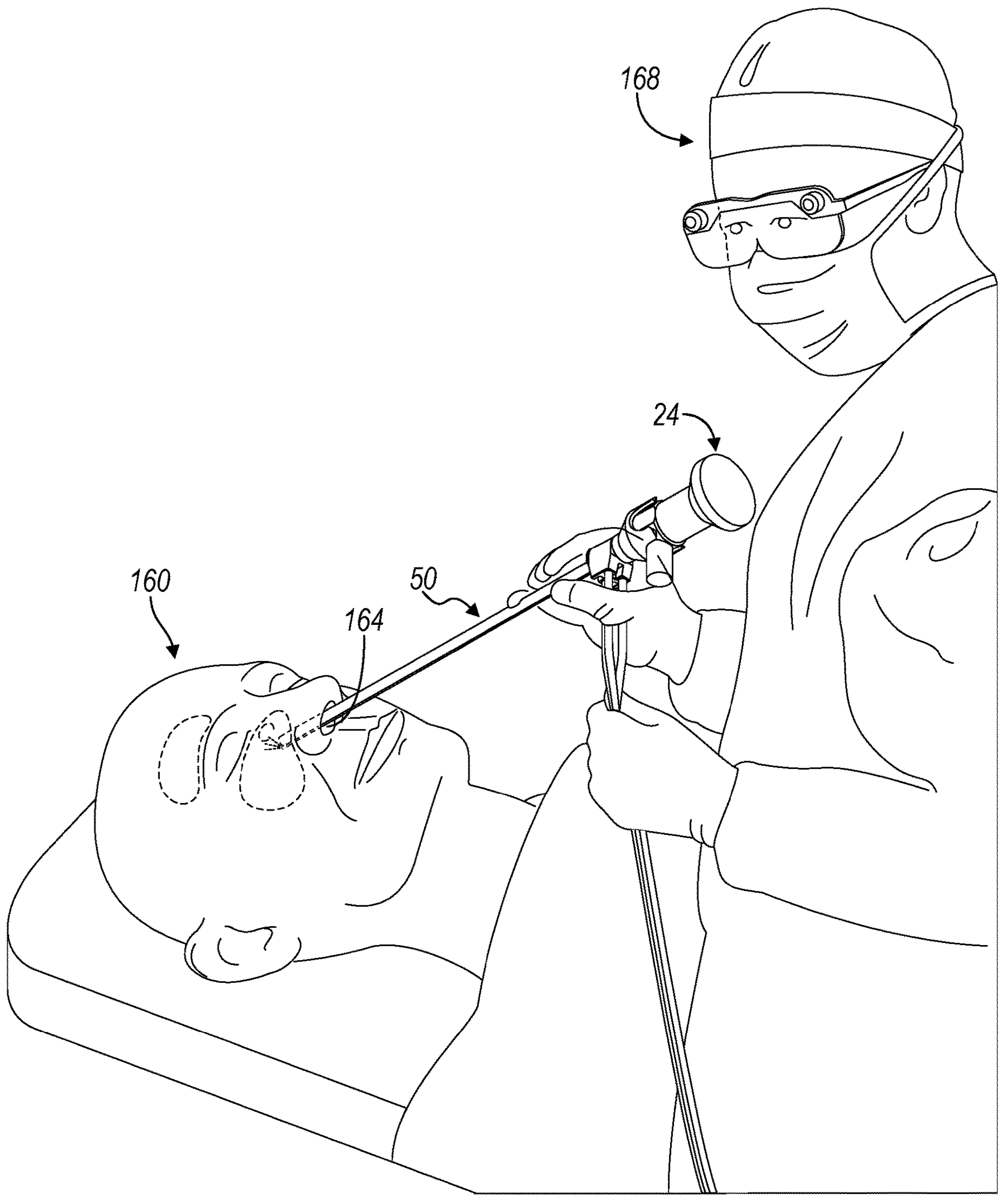
FIG. 2 is a partial environmental view of a scope with a sheath being used, according to various embodiments.

Turning reference to FIG. 2, the scope and sheath system 20 may be used to view an area within a subject 160. For example, the scope 24 having the sheath assembly 50 positioned relative thereto may be passed into a nostril 164 of the subject 160. The scope 24 may be used to view the interior of the nostril through the scope 24. A user 168 may hold the scope 24 and/or the sheath assembly 50. As discussed further herein, the user 168 may use any of the selected inputs, such as the input 140, to operate the control system or controller 82 to irrigate a portion within the subject 160, suction within the subject 160, and/or cleanse the lens or terminal end 40 of the scope 24. The user 168, therefore, may perform a procedure within the subject 160 efficiently and effectively with the assistance of cleaning an area within the subject 160, cleaning or rinsing a portion of the scope 24, and/or removing a portion of material from within the subject 160. It is understood, however, that at least one of the features need not be provided. For example, the system 82 may not provide suction or a vacuum through the sheath 50 relative to the scope 24. Nevertheless, the control system 82 may provide or deliver a selected liquid or fluid for performing selected portions relative to the subject 160, such as irrigating or lavaging within the subject 160 and/or cleaning or cleansing the terminal end 40 of the scope 24.

The sheath assembly 50, with reference to FIG. 3A and FIG. 3B, will be described in further detail here. The sheath assembly 50 may include various portions, such as those described above, including the outer scope tube 74. The tube 74 may include a wall 172 that defines an outer surface 174 and an interior surface 178. The inner surface 178 may define or form a bore or passage through which the scope body 36 may pass. The inner surface 178, therefore, may define a through-bore though the tube 74.

The sheath tube 74 may be connected to the connection region 70 that includes a first member or tube connection portion 182. The tube connection portion 182 may include a distal end or flange 184 that defines an internal bore or passage 188. The sheath tube 74, therefore, may be fixed to and/or in the inner bore 188. Generally, a proximal end 192 of the sheath tube 74 may be connected at or within the bore 188 and/or formed therewith. The first member 182 may further include a bore 196 into which or at which a proximal end 200 of the lavage tube 78 may be connected. The lavage tube 78 may include a wall 204 that extends from the proximal end 200 to a distal end 208. The lavage tube, therefore, may also define or form a bore or through-bore and passage therethrough. The distal end 208 may engage or be received in or is operable with a directing member or portion 212 at or near a distal end 216 of the sheath tube 74. Further, the lavage tube 78 is generally formed or placed exterior to the scope sheath tube 74.

The first connection or directing member 182 may further have a plurality of seal engaging regions or portions or seal portions 220, 224, 228. Each of the seal portions 220-228 may seal within or relative to a second fluid directing or member 232 of the connection portion 70. Further, in various embodiments, seal members, such as O-rings, may be engaged within the seal regions 220-228. For example, in various embodiments, seal members 236, 240, and 244 may be respectively engaged in the seal regions 220-228.

The first member 182, therefore, may be received within a bore or passage 250 of the second member 232. The bore 250 may be formed by an outer wall or body portion 254 of the second member 232. The second member 232, therefore, as discussed further herein, may seal relative to various portions of the first member 182. The second member 232 may further include connections for paths formed through and/or by the first member 182, the second member 232, the sheath tube 74, and/or the lavage tube 78. The second member 232, for example, may include the lavage connection 124, the lens cleaning connection 120, and/or the vacuum connection 128.

As discussed further herein, the second member 232, therefore, may provide the direct connections from the sheath assembly 80 to the various pumps and/or vacuums as discussed above. The sheath assembly 50 may further include the scope engaging portion or scope body engaging portion 54. The scope body engaging portion 54 may include one or more of the depressions 58 to assist in engaging or holding the sheath assembly 50 relative to the scope 24. The scope engaging portion 54 may further include a through bore 260 that is formed or defined near a proximal end of the body 54. A sealing member, such as an O-ring 264, may be sealed between the first member 182 and a wall 268 of the scope engaging portion 54. As discussed further herein, therefore, the scope tube 36 may pass through the bore 260 and be sealed relative to the first and second fluid directing members 182, 232 with the seal member 264. As discussed further herein, therefore, fluid will generally not pass toward or near the light directing portion or light post 32 of the scope assembly 24.

Figures 3A, 3B:
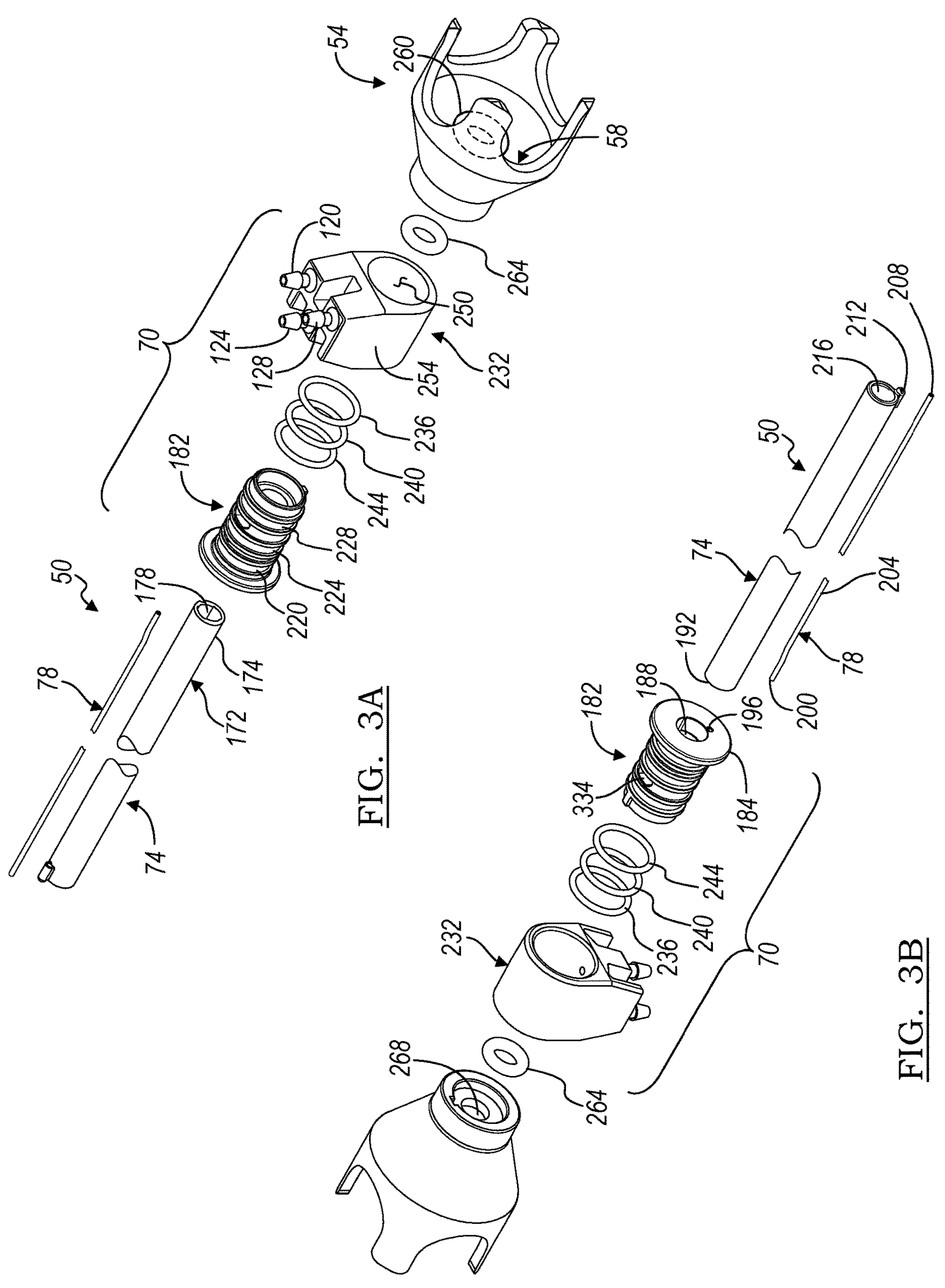
FIG. 3A is an exploded first perspective view of a sleeve assembly, according to various embodiments.
FIG. 3B is an exploded second perspective view of the sleeve assembly of FIG. 3A.
Figure 4:
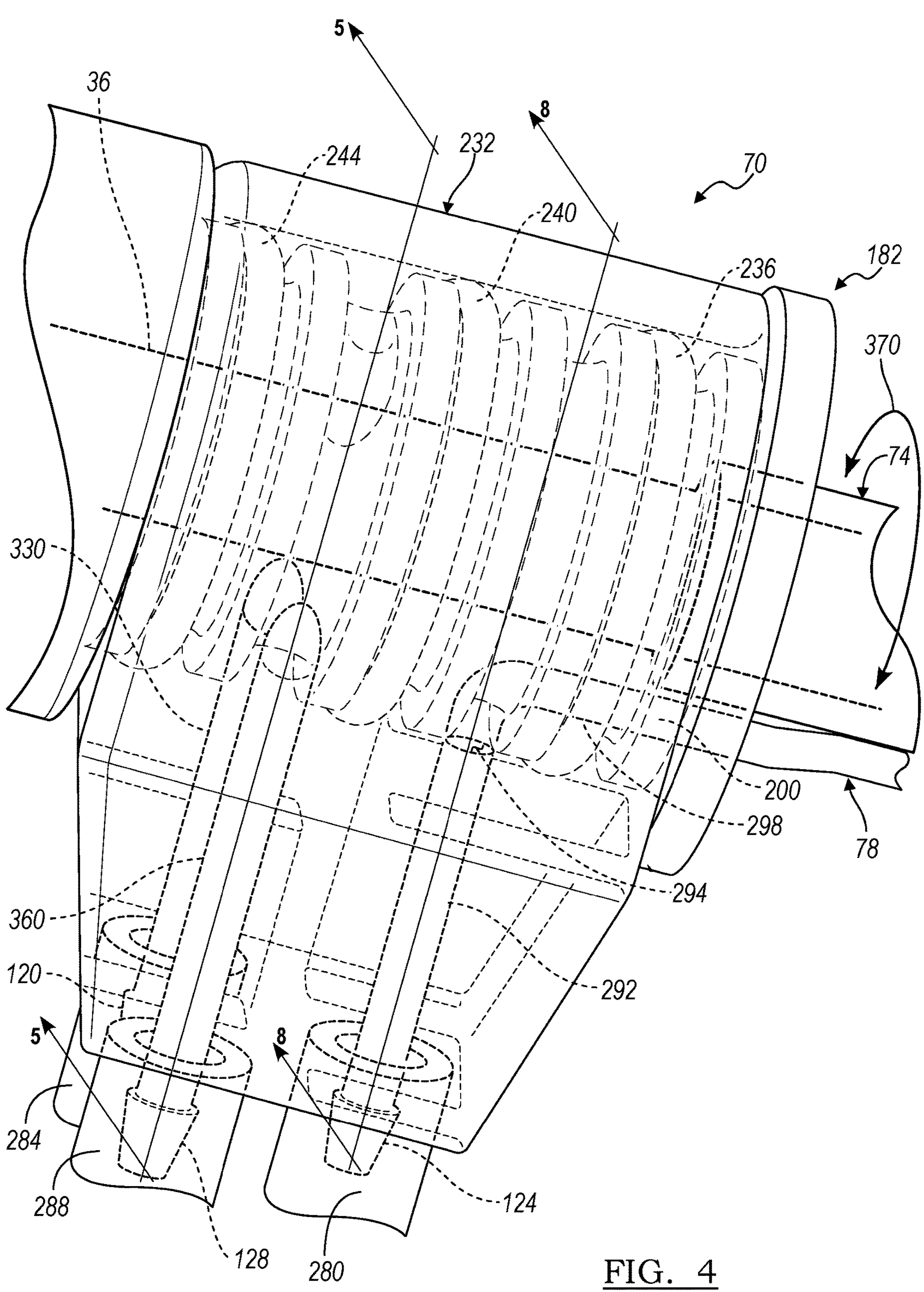
FIG. 4 is a detail partial detailed view of the sleeve and scope assembly, according to various embodiments.

With continuing reference to FIG. 3A and FIG. 3B, and further reference to FIG. 4, the fluid directing portion 70 is illustrated in detail with the scope tube 36 passing through the fluid directing area or portion 70 and the sheath tube 74. The scope tube 36 may be passed through the fluid directing portion 70, as discussed above. The fluid directing portion 70 includes the internal or first member 182 and the external or second member 232. The sealing portion 236-244 may separate to seal various portions of the fluid directing area 70 relative to one another. Accordingly, as illustrated in FIG. 4, the various connection hubs or portions may be connected to fluid transfer lines. The fluid transfer lines may include a lavage transfer line 280 that may be connected to the lavage connection 124. Further, a fluid collection line 284 may be connected to the lens cleaning barb or connection 120 and a third fluid connection 288 may be connected to the vacuum connection 128.

As illustrated in FIG. 4, the lavage connection 124 connected to the inlet 280 may be provided or provide fluid through an internal passage or path 292 formed in the second connector member 232. With continuing reference to FIG. 4 and additional reference to FIG. 5 and FIG. 5A, the internal passage 292 may be provided in various configurations, such as a substantially vertical and/or angled configuration. Regardless, the internal passage 292 may direct fluid to a second passage region 294 that may be formed or defined between the external or second fluid directing member 232 and the first directing member 182. The passage 294 may be formed or defined as a space between the two members 232, 182. Further, the sealing member or portions 236, 240 may further define or assist in defining the region. The first directing member 182 may also include a passage or through area that connects to an internal bore 298 that may receive the proximal end 200. The lavage tube 78 may then allow fluid to pass through the lavage tube 78, such as in a through bore or cannula formed therein. Accordingly, fluid may be provided from a fluid source, such as the source 110 and pumped through the pump 98 through the inlet tube 280. The various connections and passaged in the fluid directing members 182, 232 allow the fluid to then be directed to the proximal end 200 of the lavage tube 78.

Figures 5, 5A:
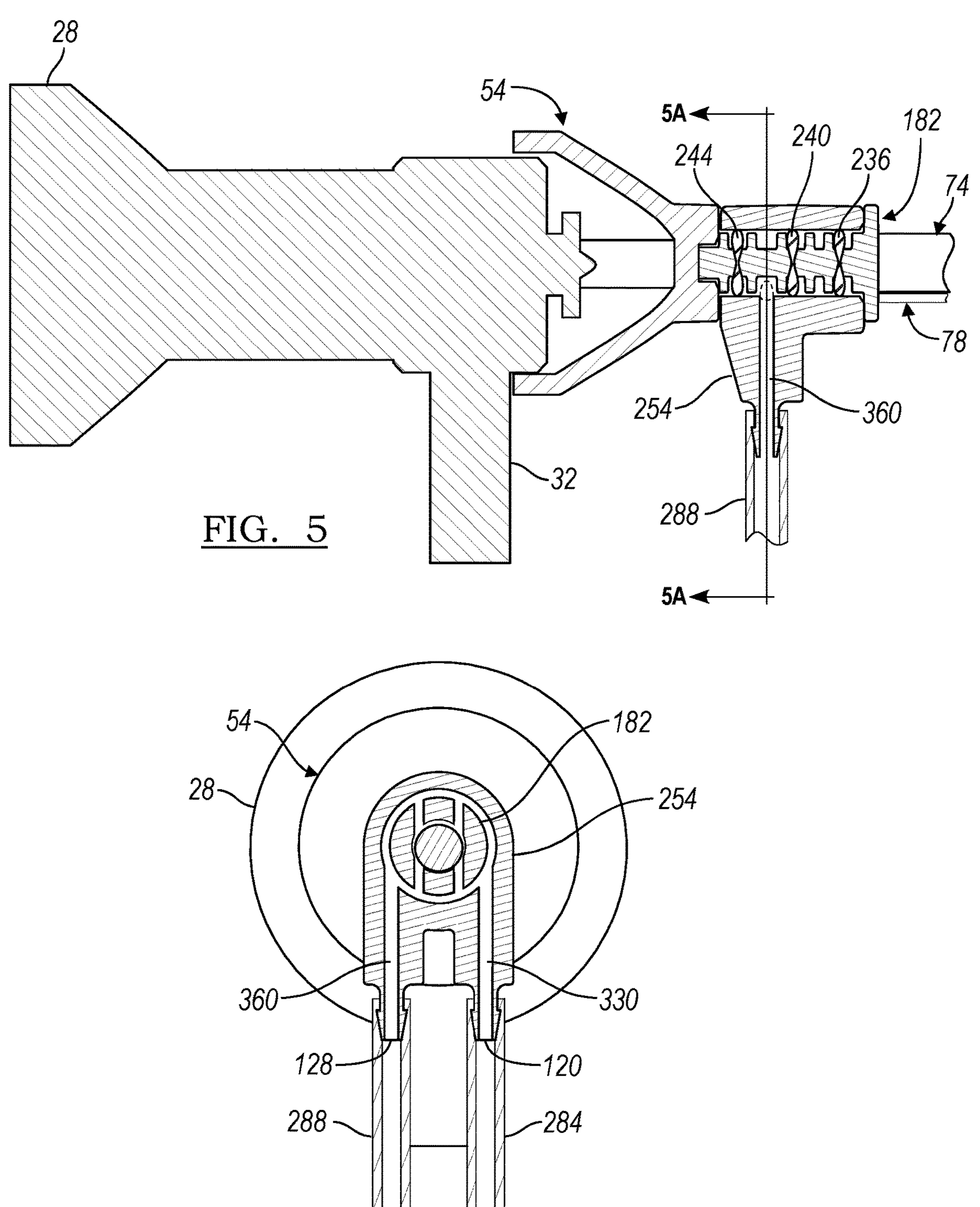
FIG. 5 is a detail cross-sectional view taken along lines 5-5 of FIG. 4.
FIG. 5A is a cross-sectional view taken along lines 5A-5A of FIG. 5.
Figures 6, 7:
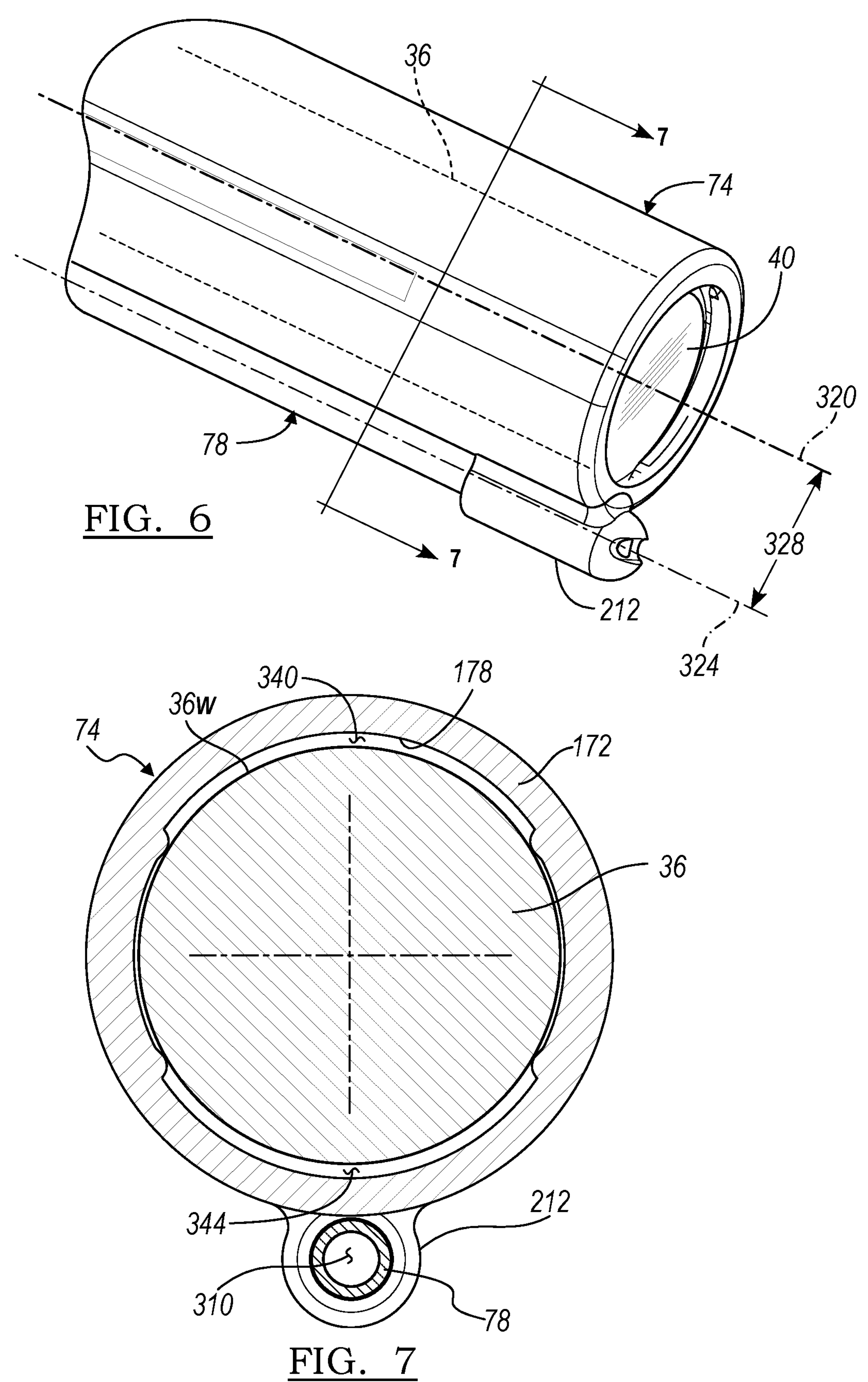
FIG. 6 is a detail rear perspective view of the sleeve and scope assembly, according to various embodiments.
FIG. 7 is a cross-sectional view taken along lines 7-7 of FIG. 6.

With continuing reference to FIGS. 4 and 5, and additional reference to FIG. 6, the lavage tube 78 may include or define an internal cannula or passage 310 that allows fluid to pass therethrough. The lavage tube 78 may then be held or terminate in a directing portion or section 212 of the sleeve assembly 50. As illustrated in FIG. 6, the scope tube 36 may be positioned within the sleeve tube 74. The lavage tube 78 is provided external to the or away from the scope tube 36. Therefore, the lavage tube 78 may generally be positioned off-axis of the scope tube. Generally, the scope tube 36 may extend along an axis 320. The lavage tube 78 may extend along an axis 324. As illustrated in FIG. 6, therefore, the axis 320 and 324 may be substantially spaced part but parallel along a path thereof. In various embodiments, however, as discussed herein, the scope 24, such as the distal end 40, thereof, may be formed of an angle relative to the axis 320. Nevertheless, the lavage tube 78 may be provided a distance, such as a distance 328 from the central axis 320 of the scope tube 36.

The flow directing portion 70, as illustrated in FIG. 4, may further allow or direct fluid relative to the scope tube 36, such as within the sleeve tube 74. Turning reference to FIG. 4, for example, the lens cleaning connection 120 that is connected to the lens cleaning tube 284, may have fluid provided therethrough, such as by operation of the pump 98. It is understood that the control system 82 may include two pumps, such as a first and second pump to operate separately for the lavage and/or the lens cleaning as discussed further herein. In an alternative and/or additionally thereto, the single pump 98 may be sequentially operated to provide for lavage through the lavage tube 78 and/or for lens cleaning.

Figures 8, 8A:
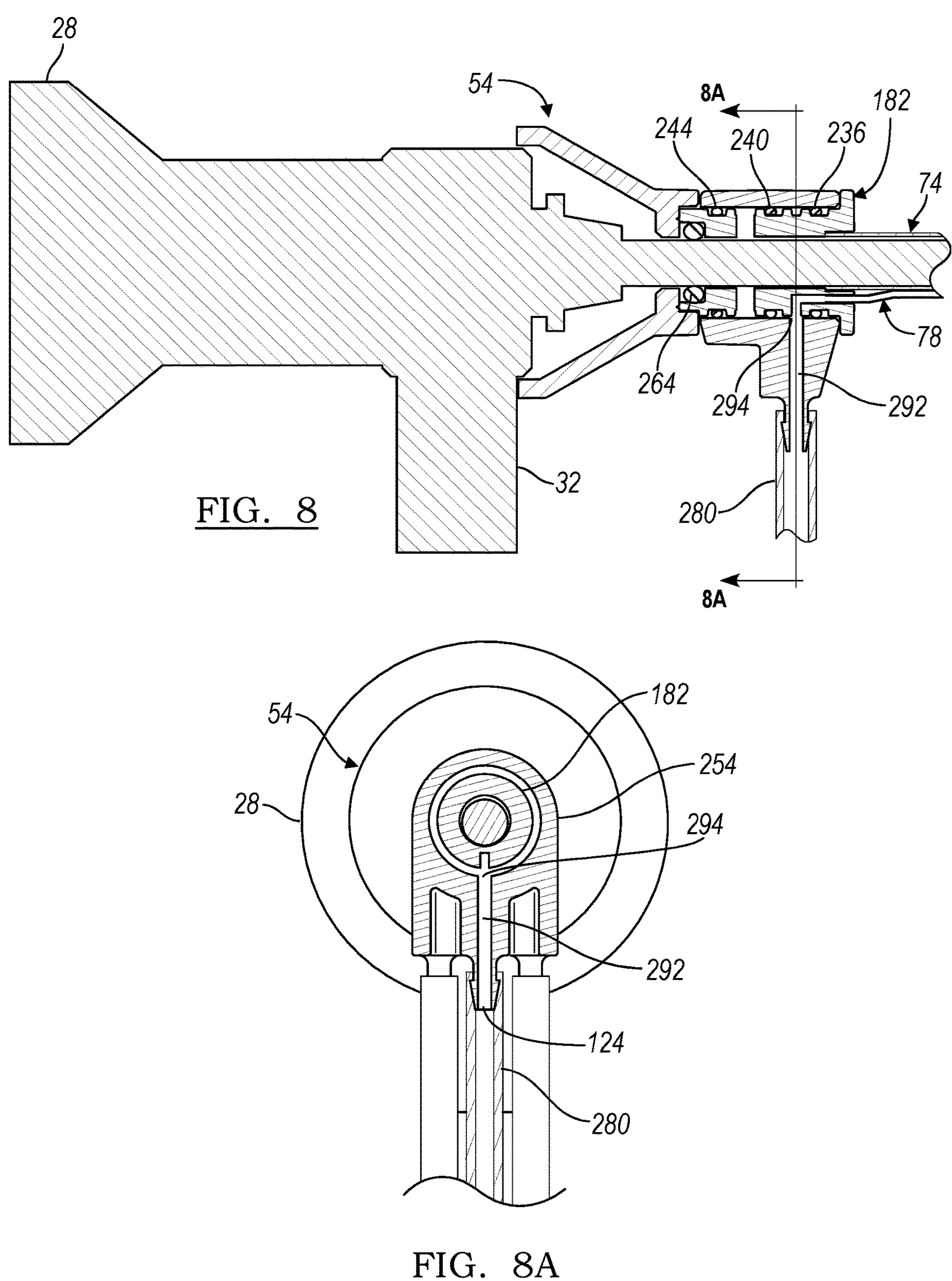
FIG. 8 is a detail cross-sectional view taken along lines 8-8 of FIG. 4.
FIG. 8A is a cross-sectional view taken along lines 8A-8A of FIG. 8.

With continuing reference to FIG. 4 and additional reference to FIG. 8 and FIG. 8A, the lens cleaning connection 120 connected to the supply line 284 may provide or direct fluid through a lens cleaning passage or path 330 in the second member 232. The fluid may then be directed through the lens cleaning passage 330 in the first member through a lens cleaning passage 334 in the first member 182. The passage 334 may then direct fluid through passages of spaces formed by the internal wall 178 of the sleeve tube 74 and the outer wall 36*w* of the scope tube 36. In various embodiments, for example, a first space or passage 340 may be formed relative to the scope tube wall 36*w* and a second passage 344 may also be formed relative to the scope wall 36*w*. The passages 340, 344 may be formed between the internal wall surface 178 of the sleeve tube 74 and the external wall surface 36*w* of the scope tube 36. The passages 340, 344 allow fluid, such as lens cleaning fluid, to pass in the spaces 340, 344 to or toward the distal end 40 of the scope tube 36 and the distal end 216 of the sleeve tube 74. It is understood that any appropriate number of the passages 340, 344 may be provided and may be formed based upon or in a selected geometry of the internal surface 178 of the sleeve tube wall 172. Regardless, the fluid may flow from the proximal end 192 of the sleeve tube to the distal end 216. At the distal end the fluid may engage or pass the distal end 40 of the scope tube 36. As the fluid passes the distal end 40 of the scope tube 36, the fluid may cleanse the distal end 40. The distal end 40 may include a lens or objective portion of the scope 24 and, therefore, cleaning the distal end 40 may assist in viewing the area of the subject 160.

In various embodiments, the fluid directing portion 70 may further include the vacuum connection 128. The third fluid line 288 may, therefore, be connected to the vacuum source or suction source 132. The system 82 may operate the valve 102 to open the valve and allow access of the vacuum connection 128 to the vacuum 132 through the connection line 288.

The vacuum connection 128 may be connected to or directed through a passage or path 360 formed in the second connection portion or directing portion 232. The internal passage 360 may also pass through the connection or passage 334 formed in the first directing member 182. The bore 334 may be formed in the first directing member 182 between the seal portions 244, 240. A channel may be formed in the first directing member 182 to allow the through portion 334 to have access or act upon the entire volume defined between the seal portions 240, 244 and the first directing member 182 and the second directing member 232. Therefore, the fluid through the tube or line 284 may pass through the bore 334 and the vacuum formed through the vacuum tube 288 may also pass through the bore 334.

As the vacuum may be formed through the bore 334, the vacuum may also be formed through the passages or spaces 340, 344, as discussed above. Therefore, the passages 340, 344 may be provided to either direct a fluid toward the distal end 40 of the scope tube 36 and/or the distal end 216 of the sleeve tube 74 and/or used to draw a vacuum relative to the distal ends 40, 216. The directing portion 70, therefore, may be provided to direct both a fluid to the distal end 216 of the sleeve tube 74 and/or a vacuum relative to the distal end 216 of the sleeve tube 74.

The sleeve tube 74 may be fixed to the first directing member 182, as discussed above. The first directing member 182 may also be fixed or connected to the scope attaching body 54. As discussed above, the scope attaching body 54 may be fixed relative to the scope 24, such as through the positioning of the light tube or light source 32 with the passage or depression 58. The various supply lines 280-288, however, may be connected to the control assembly 82 or portions relative thereto. Therefore, during use of the scope 24, the user 168 may attempt to move or manipulate the scope 24 for viewing selected portions of the subject 160. The seals and seal portions of the first member 182 relative to the second directing member 232 may allow the second directing member 232 to rotate relative to the first directing member 182. That is, during use the passages from the supply lines 280-284 to the selected portions, such as the lavage tube 78 and/or the passages 340, 344 through the sleeve tube 74, may be maintained while the second directing member 232 is able to rotate, such as generally in the direction of the double headed arrow 370, relative to the first directing member 182 and the axis 320. Therefore, the supply lines 280-288 may be positioned for efficient or ease of operation of scope 24.

Figure 9:
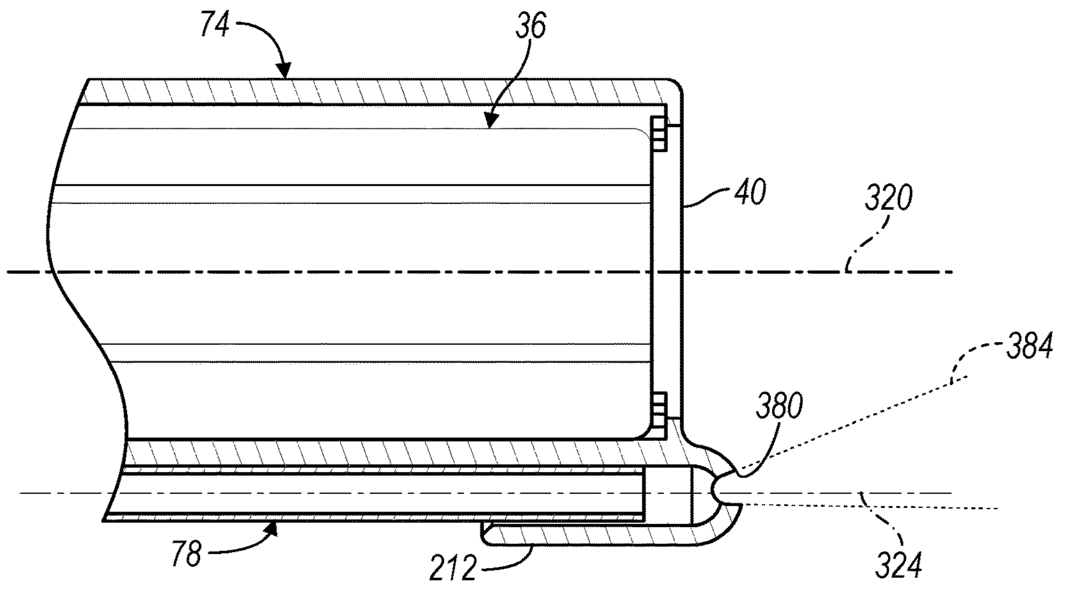
FIG. 9 is a detail distal partial cross-sectional view of a scope and tube assembly, according to various embodiments.

The sleeve assembly 50, as discussed above, may be used with the scope assembly 24, as also discussed above. With continuing reference to FIGS. 1-8, and with further reference to FIG. 9, the scope tube 36 may include the distal end 40 that is positioned within the sleeve tube 74. As discussed above, the axis 320 of the scope tube 36 may be aligned or parallel with the access 324 of the lavage tube 78. The directing portion 212 may include a directing port 380 that is also substantially aligned with the axis 324. Therefore, lavage fluid directed through the directing port 380 may be substantially aligned with the axis 320. As the terminal end 40 is substantially perpendicular to the axis 320, the area for lavage may generally be defined by the cone 384 and is generally substantially viewable or directly in front of the viewing area of the terminal end 40.

Figure 10:
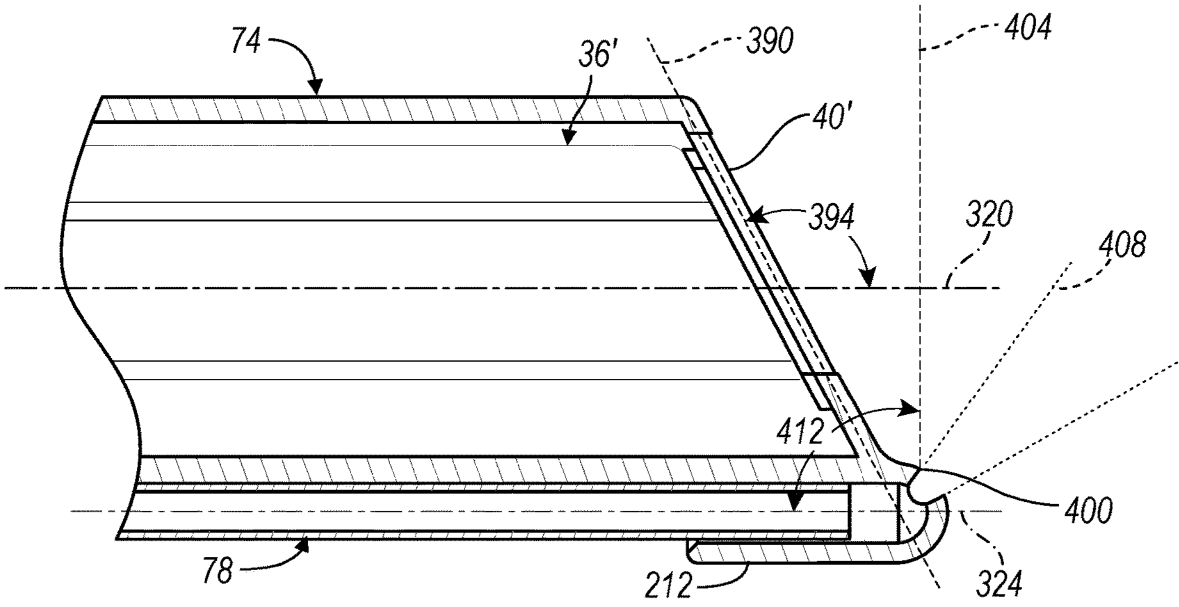
FIG. 10 is a detail partial cross-sectional view of a scope and sleeve assembly, according to various embodiments.

With continuing reference to FIGS. 1-9 and additional reference to FIG. 10, however, in various embodiments, the scope tube 36 may have a terminal end 40' that extends along a plane or axis 390 that defines an obtuse angle 394 relative to the axis 320 of the scope tube 36. The angle 394 may be an obtuse angle, as illustrated in FIG. 10. It is understood that the angle 394 may be any appropriate angle such as 120°, 150°, or generally between 91° and about 180°.

The lavage tube 78 may also generally extend along the axis 324 which is parallel with the axis 320. The directing portion 212 may include a directing port 400, however, that generally directs the lavage fluid into an area 404 that has a central or middle portion 408 at an angle 412 that acts in concert with the angle 394 such that the cone 404 is in the viewing area of the distal end 40 of the scope 36.

Thus, the directing port 400 may be provided to direct the lavage material into an optimal or selected position for cleaning an area being viewed by the terminal end 40, 40'. The directing port may be defined in the directing portion 212 and/or may be integrated into the lavage tube 78. Regardless, the lavage tube 78 is generally away from or exterior to the sleeve tube 74 so as not to obstruct a view of the scope 24, such as the terminal end 40, 40', during lavage or at any other time.

Figure 11:
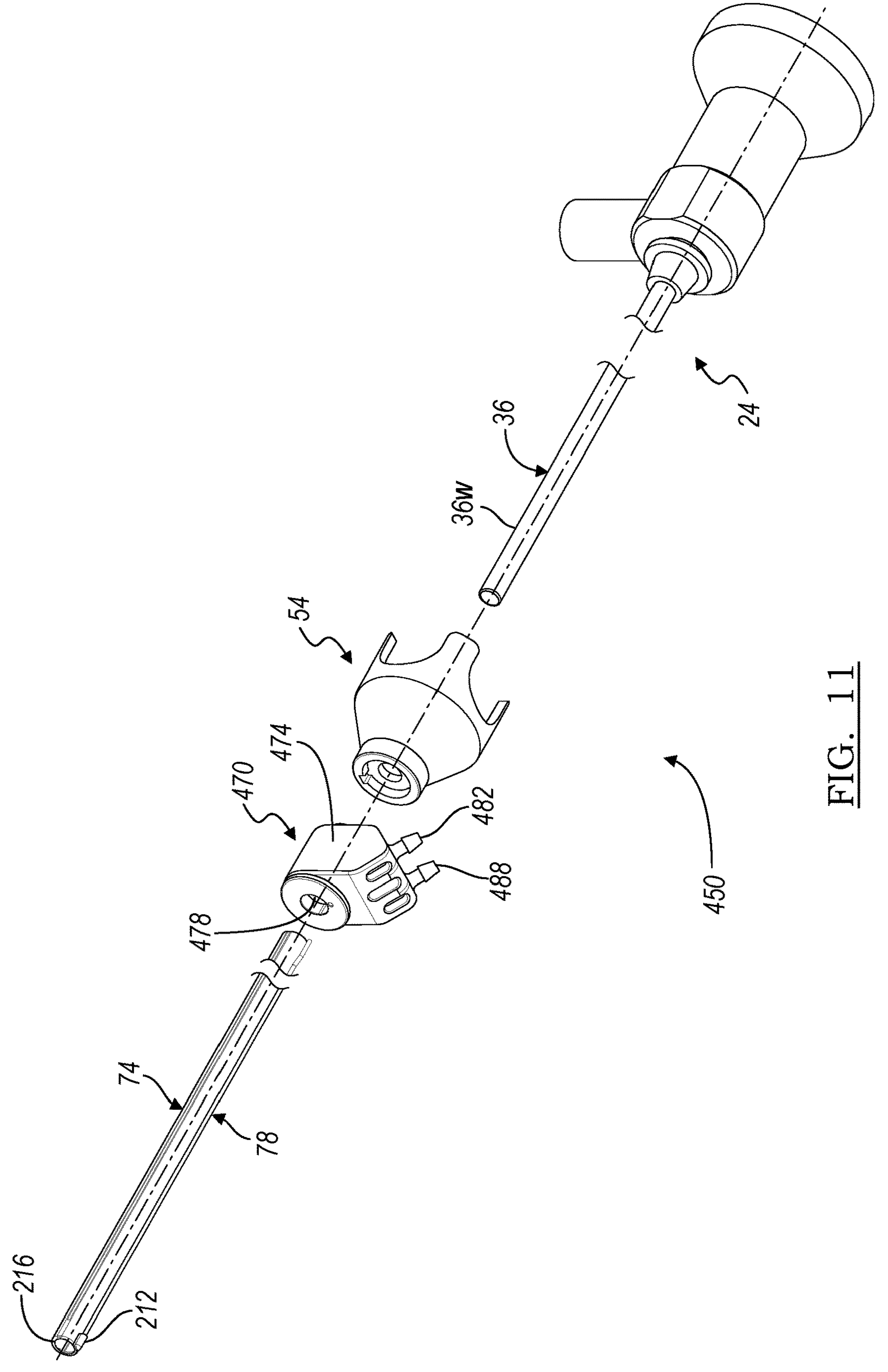
FIG. 11 is an exploded view of a scope and sleeve assembly, according to various embodiments.

Turning reference to FIG. 11, a sleeve assembly 450 is illustrated. The sleeve assembly 450 may include portions similar to those discussed above and those details will not be repeated here. The sleeve assembly 450, however, may include alternative or additional portions, which will be discussed here. Briefly, therefore, the sleeve assembly 450 may include the sleeve tube 74 and the lavage tube 78. The sleeve tube may include the directing portion 212 at or near the terminal end 216. Further the sleeve tube 74 may include the proximal end 192. The sleeve assembly 450 may further include the scope engaging portion or member 54 that may engage or be connected with the scope 24. The scope 24 may include portions substantially similar to those as discussed above.

The sleeve assembly 450, however, may include a fluid directing portion 470. The fluid directing portion 470 may include an external directing portion 474 and an internal directing portion 478. The external directing portion may include a first connection of a lavage connection 482 and a lens cleansing connection 488. The fluid directing portion 470, therefore, may not include a vacuum or suction connection. The fluid directing portion 470 may include passages and seals similar to the fluid directing portion 70, as discussed above. However, the external portion 474 may include one less connection as opposed to the external or second portion 232 as discussed above. The first or internal portion 478 may include portions that are substantially similar or identical to the first directing member 182 as discussed above. For example, to allow for passage of the lens cleansing material through the passages 340, 344 formed between the internal surface 178 of the sleeve tube 74 and the wall 36*w* of the scope tube 36. Similarly, the fluid directing portion 470 may include passage portions to allow passage of the lavage fluid therethrough to the lavage tube 78. Accordingly, the sleeve assembly 450 may not include a suction or vacuum passage but only include the fluid input or directing portions, as discussed above.

Accordingly, the sleeve assembly, according to various embodiments, may include selected directing portions. The sleeve assembly may include all of a lavage path, a lens-cleaning path, and a suction path. In various embodiments, the sleeve assembly may define only a lavage pathway and a lens-cleaning pathway without a suction pathway. Further, it is understood that the sleeve assembly may also define only a lavage pathway and a suction pathway without a separate lens-cleaning pathway. Therefore, the passages 340, 344 may be provided to only create or allow passage of suction without also directing fluid or passing fluid therethrough.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. A sleeve system, comprising:

a first elongated member having a first through-bore, the first through-bore configured to receive a scope tube of a scope therein;

a second elongated member with a second through-bore, wherein the second elongated member is fixed relative to the first elongated member outside of the first through-bore, and wherein the first elongated member is outside of the second through-bore;

a fluid directing system having a first connection and a second connection, wherein the fluid directing system comprises a first path to the first through-bore via the first connection and a second path to the second through-bore via the second connection to direct fluid through the first through-bore and the second through-bore, respectively, wherein the first path to the first through-bore extends from the first connection annularly about a portion of a circumference of the first through-bore to the first through-bore; and a scope connector connected to the fluid directing system, wherein the first elongated member includes a wall having an inner surface, the inner surface defining the first through-bore and having a plurality of projections extending from the inner surface thereof, and wherein the scope tube is configured to be inserted into the first through-bore, and operably engage the plurality of projections to define a plurality of discrete passages extending radially between at least two of the plurality of projections and between the inner surface and an outer peripheral surface of the scope tube, each of the plurality of discrete passages enclosed by the engagement of the inner surface and the outer peripheral surface of the scope tube the plurality of discreet and enclosed passages extending along a length of the outer peripheral surface of the scope tube to a distal end thereof, the plurality of discrete and enclosed passages is configured to carry and dispense a fluid proximate the distal end of the scope tube for cleaning the scope.

2. The sleeve system of claim 1, wherein the first through-bore extends along a first axis and the second through-bore extends along a second axis;

wherein the first axis is parallel and spaced apart from the second axis.

3. The sleeve system of claim 2, further comprising:

a directing portion;

wherein the directing portion is near a distal end of the first elongated member;

wherein the directing portion directs a fluid from the second through-bore into an area viewable through the first through-bore.

4. The sleeve system of claim 1, wherein the fluid directing system comprises a first member and a second member;

the first member configured to rotate within the second member;

wherein the second member is fixed to the scope connector and the first member rotates relative to the scope connector.

5. The sleeve system of claim 1, further comprising:

a third path defined by the fluid directing system;

wherein the third path and the first path are both fluidly connected to the first through-bore.

6. The sleeve system of claim 5, further comprising:

a control system having an input; and a valve;

wherein the input is operable to communicate a selection via the input to open the valve and allow a vacuum to be formed in the third path.

7. The sleeve system of claim 1, further comprising:

a pump configured to pump a liquid to the fluid directing system to flow through at least one of the first path or the second path.

8. The sleeve system of claim 7, further comprising:

a control system having an input;

wherein the input is operable to communicate a selection via the input to direct a fluid from the pump to at least one of the first path or the second path.

9. A sleeve system, comprising:

a first elongated member extending from a first end to a second end and having a first through-bore defined by an inner surface of a wall and configured to receive a scope tube of a scope therein, a plurality of projections extending from the inner surface and configured to operably engage an outer surface of the scope tube such that the receipt of the scope tube and the plurality of projections within the first through-bore defines a plurality of discrete passages extending radially between at least two of the plurality of projections and the wall and the outer surface of the scope tube, each of the plurality of discrete passages enclosed by the engagement of the inner surface and the outer peripheral surface of the scope tube when the scope tube is received within the first through-bore, the plurality of discreet and enclosed passages extending along a length of the outer peripheral surface of the scope tube to a distal end thereof;

a directing portion positioned near the second end;

a second elongated member with a second through-bore, wherein the second elongated member is fixed to an exterior surface of the wall outside the second through-bore such that the first elongated member is outside the second through-bore, and wherein the second elongated member terminates at the directing portion;

a scope connector configured to engage at least a portion of the scope; and a fluid directing system having a first member fixed to the scope connector and a second member moveable relative to at least one of the first member or the scope connector;

wherein the second member of the fluid directing system further comprises at least a first connection and a second connection; and wherein the fluid directing system comprises a first path to the first through-bore via the first connection and a second path to the second through-bore via the second connection, wherein the first path to the first through-bore extends from the first connection annularly about a portion of a circumference of the first through-bore to the first through-bore, and wherein the plurality of discrete and enclosed passages is configured to carry and dispense a fluid proximate the distal end of the scope tube for cleaning the scope.

10. The sleeve system of claim 9, further comprising:

a first pump to pump a first fluid to the first connection;

a second pump to pump a second fluid to the second connection; and a control system configured to control the first pump and the second pump to selectively pump the first fluid or the second fluid.

11. The sleeve system of claim 10, wherein the control system includes an input to receive user input from a user regarding operation of the first pump or the second pump.

12. The sleeve system of claim 9, further comprising:

a third path defined by the fluid directing system;

wherein the third path and the first path are both fluidly connected to the first through-bore.

13. The sleeve system of claim 12, further comprising:

a control system having an input; and a valve;

wherein the input is operable to communicate a selection via the input to open the valve and allow a vacuum to be formed in the third path.

* * * * *